United States Patent
Mochly-Rosen et al.

(10) Patent No.: US 7,560,241 B2
(45) Date of Patent: Jul. 14, 2009

(54) METHODS AND COMPOSITIONS FOR MODULATING MITOCHONDRIAL ALDEHYDE DEHYDROGENASE-2

(75) Inventors: Daria Mochly-Rosen, Menlo Park, CA (US); Che-Hong Chen, Fremont, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 338 days.

(21) Appl. No.: 11/008,482

(22) Filed: Dec. 8, 2004

(65) Prior Publication Data

US 2005/0171043 A1 Aug. 4, 2005

Related U.S. Application Data

(60) Provisional application No. 60/528,441, filed on Dec. 9, 2003.

(51) Int. Cl.
*G01N 33/53* (2006.01)
*G01N 33/566* (2006.01)

(52) U.S. Cl. .................... 435/7.1; 435/7.4; 435/7.9; 435/174; 436/501; 424/94.1

(58) Field of Classification Search ............... None
See application file for complete search history.

(56) References Cited

U.S. PATENT DOCUMENTS

2002/0150984 A1  10/2002  Mochly-Rosen
2002/0168354 A1  11/2002  Mochly-Rosen

FOREIGN PATENT DOCUMENTS

WO    WO 03/075832    9/2003

OTHER PUBLICATIONS

Loomes and Kitson (Biochemical Journal, 1989, vol. 261, No. 1. pp. 281-284).*
Inagaki et al. (2003) *Circulation* 108:869-875.
Mackay and Mochly-Rosen (2001) *Cardiovasc. Res.* 50:65-74.
Vallarai, Robert C. et al., "Interaction of Mg2+with Human Liver Aldehyde Dehydrogenase" The Journal of Biological Chemistry, vol. 259, No. 8, Apr. 25, 1984, pp. 4922-4926.
Chen, Mei, et al. "Enzymatic Conversion of Retinaldehyde to Retinoic Acid by Cloned Murine Cystolic and Mitcochondrial Aldehyde Dehydrogenases"Molecular Pharmacology, vol. 46, No. 1, 1994, pp. 88-96.
Bogdanova, Anna V. et al. Mapping of the immunodominant regions of the NAD-dependent formate dehydrogenase. FEBS Letters, vol. 260, No. 2, Jan. 29, 1990, pp. 297-300.
Dandre, F. et al. The frequency of the mitochondrial aldehyde dehydrogenase I2(atypical) allele in Caucasian, Oriental and African Black populations determined by the restriction profile of PCR-amplified DNA. Molecular and Cellular Probes, 1995, vol. 9, pp. 189-193.
Kamino, K. et al. Deficiency in Mitochondrial Aldehyde Dehydrogenase Increases the Risk for Late-Onset Alzheimer's Disease in the Japanese Population. Biochemical and Biophysical Research Communications, vol. 273, 2000, pp. 192-196.
Kazmierczak et al., "Description of a Novel Fusion Transcript between HMCI-C, a Gene Encoding for a Member of the High Mobility Group Proteins, and the Mitochondrial Aldehyde Dehydrogenase Gene" Cancer Research, vol. 55, Dec. 15, 1995, pp. 6038-6039.
Timar, J. et al. "The Effect of Leukocyte Interleukin Injection (Multikine) Treatment on the Peritumoral and Intramural Subpopulation of Mononuclear Cells and on Tumor Epithelia: A Possible New Approach to Augmenting Sensitivity to Radiation Therapy and Chemotherapy in Oral Cancer—A Multicenter Phase I/II Clinical Trial" The Laryngoscope, vol. 113, Dec. 2003, pp. 2206-2217.
Li et al., Overexpression of Aldehyde Dehydrogenase-2 (ALDH2) Transgene Prevents Acetaldeyde-induced Cell Injury in Human Umbilical Vein Endothelial Cells, *The Journal of Biological Chemistry*, vol. 279, No. 12, pp. 11244-11252.
Dong "Alcohol and Congestive Heart Failure" *Annals of Internal Medicine*, 2003, vol. 138, No. 1, pp. 75-76.
Li et al., Overexpression of Aldehyde Dehydrogenase-2 (ALDH2) Transgene Prevents Acetaldeyde-induced Cell Injury in Human Umbilical Vein Endothelial Cells, *The Journal of Biological Chemistry*, vol. 279, No. 12, pp. 11244-11252, Mar. 19, 2004.
Ohsawa et al., "Deficiency in a mitochondrial aldehyde dehydrogenase increases vulnerability to oxidative stress in PC12 cells", *Journal of Neurochemistry*, 2003, vol. 84, No. 5, pp. 1110-1117.
Walsh et al., Alcohol Consumption and Risk for Congestive Heart Failure in the Framingham Heart Study, *Annals of Internal Medicine*, 2002, vol. 136, No. 3, pp. 181-191.

* cited by examiner

*Primary Examiner*—Lisa V Cook
(74) *Attorney, Agent, or Firm*—Paula A. Borden; Bozicevic, Field & Francis LLP

(57) ABSTRACT

The present invention provides screening methods for identifying agents that modulate the activity of mitochondrial aldehyde dehydrogenase-2 (AldDH2), as well as agents identified by the screening methods. The present invention further provides methods of reducing ischemic tissue damage or free-radical induced damage in an organ, the methods generally involving contacting the organ with an agent that increases AldDH2 levels and/or activity. The present invention further provides methods of treating solid tumors, the methods generally involving administering an agent that decreases AldDH2 levels and/or activity.

8 Claims, 9 Drawing Sheets

METHODS AND COMPOSITIONS FOR MODULATING MITOCHONDRIAL ALDEHYDE DEHYDROGENASE-2

CROSS-REFERENCE

This application claims the benefit of U.S. Provisional Patent Application No. 60/528,441 filed Dec. 9, 2003, which application is incorporated herein by reference in its entirety.

STATEMENT REGARDING FEDERALLY SPONSORED RESEARCH

The U.S. government may have certain rights in this invention, pursuant to grant no. AAA11147 awarded by the National Institutes of Health.

FIELD OF THE INVENTION

The present invention is in the field of ischemic tissue damage, and in particular use of modulators of mitochondrial aldehyde dehydrogenase 2 to modulate tissue damage due to an ischemic event.

BACKGROUND OF THE INVENTION

Tissues deprived of blood and oxygen undergo ischemic necrosis or infarction with possible irreversible organ damage. In some circumstances, such as during surgery, interruption of blood flow resulting in ischemia of some organ is unavoidable. In addition, in the case of solid tumors, it is desirable to interrupt the blood flow and actually induce ischemia. Once the flow of blood and oxygen is restored to the organ or tissue (reperfusion), the organ does not immediately return to the normal preischemic state. For example, in the case of the ischemic myocardium, reperfused postischemic non-necrotic myocardium is poorly contractile and has reduced concentrations of high energy nucleotides, depressed subcellular organelle function and membrane damage that resolves only slowly.

There is a need in the art for methods of reducing tissue damage due to ischemia and treating solid tumors. The present invention addresses these needs.

Literature

U.S. Pat. No. 6,165,977; U.S. Patent Publication Nos. 20020168354 and 20020150984; Inagaki et al. (2003) Circulation 108: 869-875; Mackay and Mochly-Rosen (2001) *Cardiovasc. Res.* 50: 65-74.

SUMMARY OF THE INVENTION

The present invention provides screening methods for identifying agents that modulate the activity of mitochondrial aldehyde dehydrogenase-2 (AldDH2), as well as agents identified by the screening methods. The present invention further provides methods of reducing ischemic tissue damage or free-radical induced damage in an organ, the methods generally involving contacting the organ with an agent that increases AldDH2 levels and/or activity. The present invention further provides methods of treating solid tumors, the methods generally involving administering an agent that decreases AldDH2 levels and/or activity.

DEFINITIONS

Figure 1:
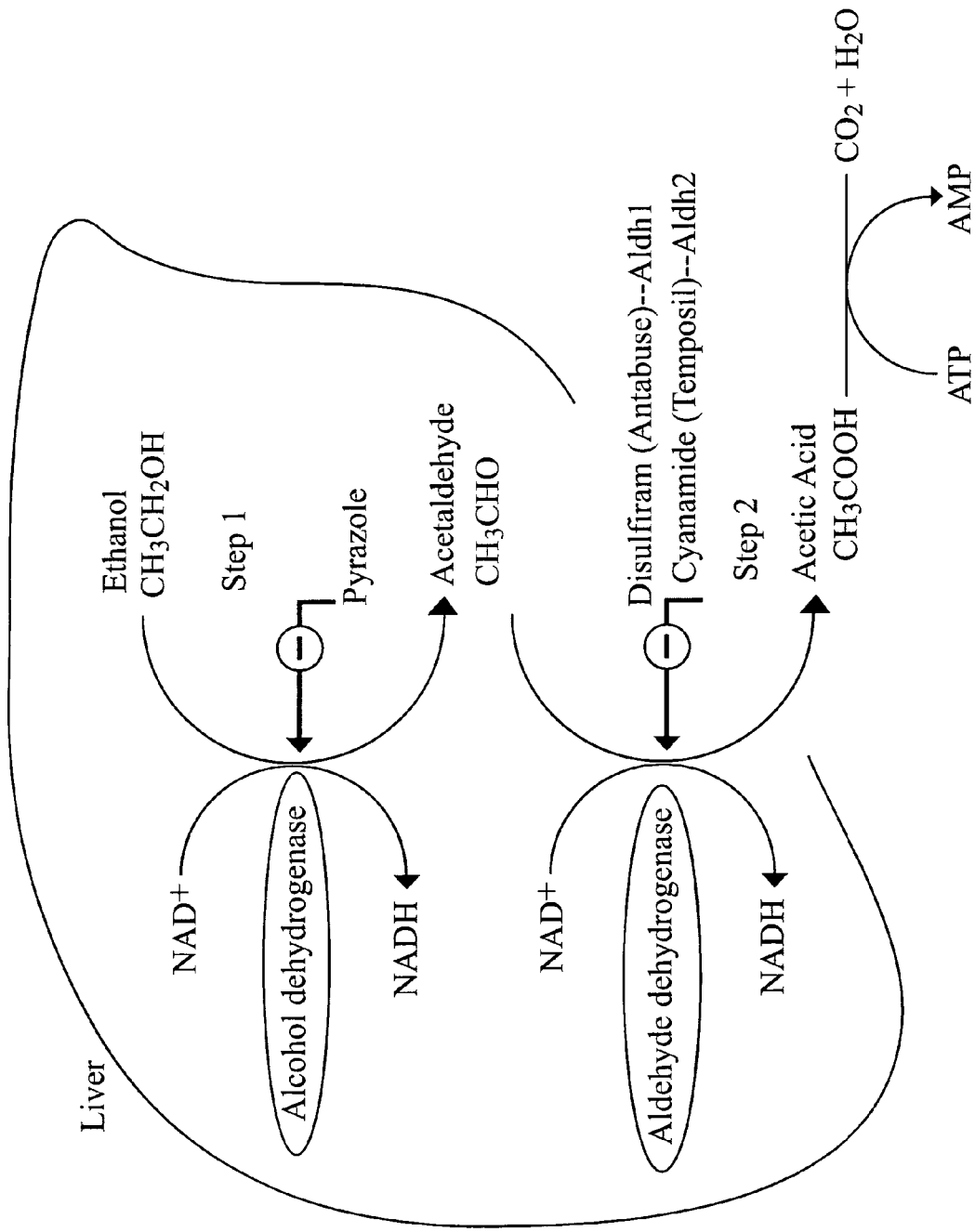
FIG. 1 is a schematic representation of ethanol metabolism in the liver, and the role of AldDH2 in the process.

The term "agent" includes any substance, molecule, element, compound, entity, or a combination thereof. The term "agent" includes, but is not limited to, e.g., small organic molecules; small inorganic molecules; and macromolecules such as polysaccharides, polynucleotides, polypeptides, glycoproteins, lipoproteins, and the like. An "agent" is a natural product, a synthetic compound, a semi-synthetic compound, or a chemical compound, or a combination of two or more substances. Unless otherwise specified, the terms "agent," "candidate agent," "test agent," "substance," and "compound" are used interchangeably.

The term "analog" is used herein to refer to a molecule that structurally resembles a molecule of interest but which has been modified in a targeted and controlled manner, by replacing a specific substituent of the reference molecule with an alternate substituent. Compared to the starting molecule, an analog may exhibit the same, similar, or improved utility. Synthesis and screening of analogs, to identify variants of known compounds having improved traits (such as higher potency at a specific receptor type, or higher selectivity at a targeted receptor type and lower activity levels at other receptor types) is an approach that is well known in pharmaceutical chemistry.

The terms "individual," "host," "subject," and "patient," used interchangeably herein, refer to a mammal, including, but not limited to, murines, felines, simians, humans, mammalian farm animals, mammalian sport animals, and mammalian pets.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an agent" includes a plurality of such agents and reference to "the AldDH2 polypeptide" includes reference to one or more AldDH2 polypeptides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides screening methods for identifying agents that modulate the activity of mitochondrial aldehyde dehydrogenase-2 (AldDH2), as well as agents identified by the screening methods. The present invention further provides methods of reducing ischemic tissue damage or free-radical induced damage in an organ, the methods generally involving contacting the organ with an agent that increases AldDH2 levels and/or activity. The present invention further provides methods of treating solid tumors, the methods generally involving administering an agent that decreases AldDH2 levels and/or activity.

The present invention is based in part on the observation that mitochondrial AldDH2 mediates cardioprotection by exposure of the organ to low levels of ethanol, or direct activation of epsilon protein kinase C (εPKC). It was observed that mitochondrial AldDH2 is activated by ethanol and by εPKC activation, and that the increase in mitochondrial AldDH2 catalytic activity is inversely correlated to the infarct size. The data indicate that mitochondrial AldDH2 is a key mediator of cardioprotection from ischemia and reperfusion of the heart.

Screening Methods

The present invention provides methods of identifying agents that modulate mitochondrial aldehyde dehydrogenase-2 (AldDH2) levels and/or activity. The term "modulate" includes "increase" and "decrease." Of particular interest in some embodiments are methods of identifying agents that increase AldDH2 activity and/or levels. Agents that increase AldDH2 activity and/or levels are expected to be useful in treating ischemia. Of particular interest in some embodiments are agents that reduce AldDH2 activity and/or levels. Agents that inhibit AldDH2 activity are expected to be useful as anti-solid tumor treatment.

In some embodiments, the invention provides methods for identifying agents that modulate AldDH2 enzymatic activity. The methods generally involve contacting a sample comprising AldDH2 with a test agent; and determining the effect, if any, of the test agent on AldDH2 activity. Typically, the sample also includes a substrate for AldDH2.

As used herein, the term "determining" refers to both quantitative and qualitative determinations and as such, the term "determining" is used interchangeably herein with "assaying," "measuring," and the like.

In some embodiments, the invention provides methods for identifying agents that increase or decrease a level of AldDH2 mRNA and/or protein. The methods generally involve contacting a cell that comprises a nucleic acid comprising a nucleotide sequence that encodes AldDH2; and determining the effect, if any, of the test agent on AldDH2 mRNA and/or polypeptide levels.

The terms "candidate agent," "test agent," "agent", "substance" and "compound" are used interchangeably herein. Candidate agents encompass numerous chemical classes, typically synthetic, semi-synthetic, or naturally-occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible.

Candidate agents may be small organic or inorganic compounds having a molecular weight of more than 50 and less than about 10,000 daltons, e.g., a candidate agent may have a molecular weight of from about 50 daltons to about 100 daltons, from about 100 daltons to about 200 daltons, from about 200 daltons to about 500 daltons, from about 500 daltons to about 1000 daltons, from about 1,000 daltons to about 2500 daltons, from about 2500 daltons to about 5000 daltons, from about 5000 daltons to about 7500 daltons, or from about 7500 daltons to about 10,000 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Assays of the invention include controls, where suitable controls include a sample (e.g., a sample comprising AldDH2 and substrate in the absence of the test agent; a sample comprising a cell in the absence of test agent; a cell sample in the absence of test agent; etc.). Generally a plurality of assay mixtures is run in parallel with different agent concentrations to obtain a differential response to the various concentrations.

Typically, one of these concentrations serves as a negative control, i.e. at zero concentration or below the level of detection.

A variety of other reagents may be included in the screening assay. These include reagents like salts, neutral proteins, e.g. albumin, detergents, etc., including agents that are used to facilitate optimal enzyme activity and/or reduce non-specific or background activity. Reagents that improve the efficiency of the assay, such as protease inhibitors, nuclease inhibitors, anti-microbial agents, etc. may be used. The components of the assay mixture are added in any order that provides for the requisite activity. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

The screening methods may be designed a number of different ways, where a variety of assay configurations and protocols may be employed, as are known in the art. For example, one of the components may be bound to a solid support, and the remaining components contacted with the support bound component. The above components of the method may be combined at substantially the same time or at different times.

AldDH2

The term "mitochondrial AldDH2" as used herein refers to an enzyme that catalyzes the oxidation of aldehydes to their corresponding acids in an $NAD^+$-dependent reaction. The amino acid sequences of mitochondrial AldDH2 from various species are publicly available. For example, a human mitochondrial AldDH2 amino acid sequence is found under GenBank Accession Nos. AAH02967 and NP_000681; a mouse mitochondrial AldDH2 amino acid sequence is found under GenBank Accession No. NP_033786; and a rat mitochondrial AldDH2 amino acid sequence is found under GenBank Accession No. NP_115792. The term "mitochondrial AldDH2" as used herein thus also encompasses fragments, fusion proteins, and variants (e.g., variants having one or more amino acid substitutions, addition, deletions, and/or insertions) that retain AldDH2 enzymatic activity. Specific enzymatically active AldDH2 variants, fragments, fusion proteins, and the like can be verified by adapting the methods described herein.

Variant proteins that are suitable for a subject screening method retain enzymatic activity. Conserved residues; residues that, if mutated, result in decreased enzymatic activity; and residues that may be mutated without substantially affecting enzymatic activity are known in the art and/or are readily determined by those of ordinary skill in the art. Publications discussing conserved residues; residues that, if mutated, result in decreased enzymatic activity; and residues that may be mutated without substantially affecting enzymatic activity include, e.g., Sheikh et al. ((1997) *J. Biol. Chem.* 272: 18817-18822) and Farres et al. ((1994) *J. Biol. Chem.* 269: 13854-13860).

Mitochondrial AldDH2 fusion proteins comprise AldDH2 and a heterologous polypeptide (a "fusion partner"), where the fusion partner is attached to the amino terminus or the carboxyl terminus of the AldDH2 polypeptide. Suitable fusion partners include immunological tags such as epitope tags, including, but not limited to, hemagglutinin, FLAG, and the like; proteins that provide for a detectable signal, including, but not limited to, fluorescent proteins, enzymes (e.g., β-galactosidase, luciferase, horse radish peroxidase, etc.), and the like; polypeptides that facilitate purification or isolation of the fusion protein, e.g., metal ion binding polypeptides such as 6His tags (e.g., AldDH2/6His), glutathione-S-transferase, and the like; polypeptides that provide for subcellular localization; and polypeptides that provide for secretion from a cell.

Mitochondrial AldDH2 used in the assay of the invention can be isolated from a source of the enzyme (e.g., from cells that naturally produce AldDH2), by synthetic methods, or by recombinant techniques, each of which methods are well known in the art.

Identifying Agents that Modulate AldDH2 Enzymatic Activity

In some embodiments, the invention provides methods for identifying agents that increase or decrease AldDH2 enzymatic activity. In many embodiments, such assays are cell-free in vitro assays. The methods generally involve contacting a sample (e.g., a cell-free sample) comprising AldDH2 with a test agent in vitro; and determining the effect, if any, of the test agent on AldDH2 activity. Typically, the sample also includes a substrate for AldDH2, and the co-factor $NAD^+$.

Assays for mitochondrial AldDH2 are known in the art, and any known assay can be used in a subject screening method. Examples of assays are found in various publications, including, e.g., Sheikh et al. ((1997) *J. Biol. Chem.* 272: 18817-18822) and Farres et al. ((1994) *J. Biol. Chem.* 269: 13854-13860). For example, mitochondrial AldDH2 is assayed at 25° C. in 50 mM sodium pyrophosphate HCl buffer, pH 9.0, 100 mM sodium phosphate buffer, pH 7.4, or 50 mM sodium phosphate buffer, pH 7.4, where the buffer includes $NAD^+$ (e.g., 0.8 mM $NAD^+$, or higher, e.g., 1 mM, 2 mM, or 5 mM $NAD^+$) and a substrate such as 14 µM propionaldehyde. Reduction of NAD+ is monitored at 340 nm using a spectrophotometer, or by fluorescence increase using a fluoromicrophotometer.

Figure 9:
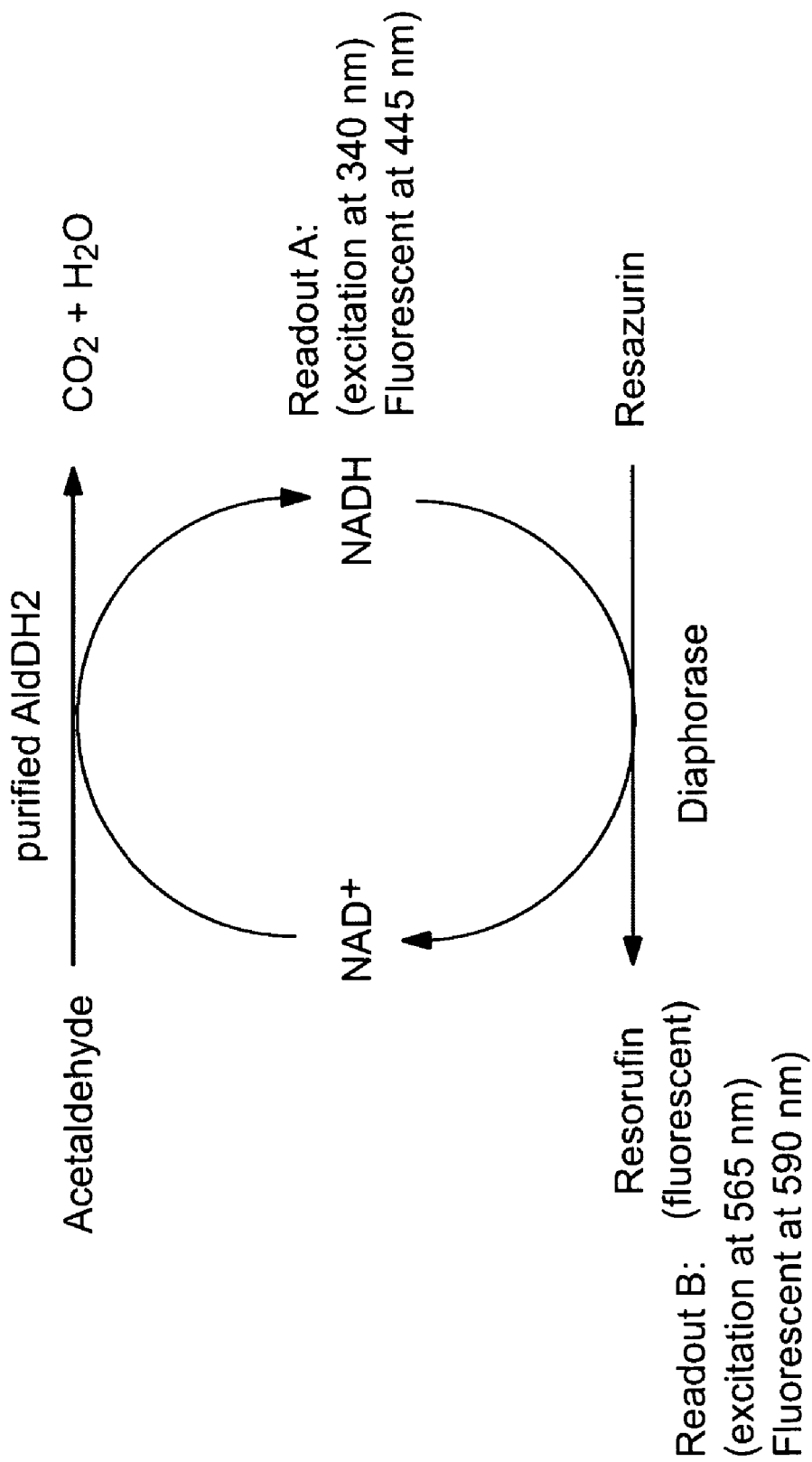
FIG. 9 depicts the principle of a fluorescent aldehyde dehydrogenase enzymatic assay.

Mitochondrial AldDH2 enzymatic activity can be assayed using a standard spectrophotometric method, e.g., by measuring a reductive reaction of the oxidized form of nicotinamide adenine dinucleotide ($NAD^+$) to its reduced form, NADH, at 340 nm, as shown schematically in FIG. 9. In a typical assay. the reaction is carried out at 25° C. in 0.1 NaPPi buffer, pH 9.5, 2.4 mM $NAD^+$ and 10 mM acetaldehyde as the substrate. Enzymatic activity is measured by a reductive reaction of $NAD^+$ to NADH at 340 nm, as depicted in FIG. 9 (Readout A). Alternative, the production of NADH can be coupled with another enzymatic reaction that consumes NADH and that provides for a detectable signal. An example of such an enzymatic reaction is a diaphorase-based reaction, which reduces resazurin to its oxidized fluorescent compound resorufin, as depicted schematically in FIG. 9. Detection of fluorescent resorufin at 590 nm provides amplified and more sensitive signals for any change in mitochondrial AldDH2 enzymatic activity (Readout B of FIG. 9).

As one non-limiting example, a 120 µl reaction mixture for mitochondrial AldDH2 enzymatic activity comprises the following components:
- 43 µl 150 mM sodium pyrophosphate (NaPPi) buffer, pH 9.0;
- 30 µl 10 mM $NAD^+$;
- 15 µl 80 mM acetaldehyde;
- 1 µl of resazurin (0.2 mg/ml in $H_2O$);
- 1 µl of diaphorase (1 unit, e.g., from *Clostridium kluyveri*);
- 2 µl of AldDH2 (e.g., 2 µl of recombinant human mitochondrial AldDH2 at (0.5-2 µg/µl); and
- 28 µl of a solution comprising an agent to be tested, which agent has been resuspended in an appropriate solvent (e.g., an aqueous solution, DMSO, and the like) (from the chemical compound library collections).

Fluorescent detection of the above-described reaction as described in Table 1:

TABLE 1

|  | Excitation | Emission | Cutoff |
| --- | --- | --- | --- |
| Channel 1 | 340 nm | 445 nm | 410 nm |
| Channel 2 | 565 nm | 590 nm | 570 nm |

This reaction can be carried out in a 96-well, a 384-well, a 1536-well micro-well plate, etc., or adapted to other screening formats.

In some embodiments, the in vitro cell-free assay will employ a purified mitochondrial AldDH2, where "purified" refers to free of contaminants or any other undesired components. Purified mitochondrial AldDH2 that is suitable for a subject screening method is at least about 70% pure, at least about 75% pure, at least about 80% pure, at least about 85% pure, at least about 90% pure, at least about 95% pure, at least about 98% pure, at least about 99% pure, or greater than 99% pure.

Purified mitochondrial AldDH2 will in some embodiments be stabilized by addition of one or more stabilizing agents, to maintain enzymatic activity. In some embodiments, a solution of purified mitochondrial AldDH2 comprises an aqueous solution of mitochondrial AldDH2 and from about 10% to about 50% glycerol, e.g., from about 10% to about 15%, from about 15% to about 20%, from about 20% to about 25%, from about 25% to about 30%, from about 30% to about 35%, from about 35% to about 40%, from about 40% to about 45%, or from about 45% to about 50% glycerol. In some embodiments, a solution of mitochondrial AldDH2 further comprises one or more of a chelating agent (e.g., EDTA or EGTA); salts such as NaCl, $MgCl_2$, KCl, and the like; buffers, such as a Tris buffer, phosphate-buffered saline, sodium pyrophosphate buffer, and the like; one or more protease inhibitors; and the like.

In some embodiments, the in vitro cell-free assay will employ a recombinant mitochondrial AldDH2. Recombinant mitochondrial AldDH2 is readily prepared in a variety of host cells such as unicellular microorganisms, or cells of multicellular organisms grown in in vitro culture as unicellular entities. Suitable host cells include bacterial cells such as *Escherichia coli*; yeast cells such as *Saccharomyces cerevisiae, Pichia pastoris, Hansenula polymorpha, Kluyveromyces lactis, Yarrowia lipolytica, Candida utilis, Schizosaccharomyces pombe*, and the like; insect cells such as *Drosophila melanogaster* cells; amphibian cells such as *xenopus* cells; mammalian cells, such as CHO cells, 3T3 cells, and the like. In some embodiments, the in vitro cell-free assay will employ a human mitochondrial AldDH2. In some embodiments, the in vitro cell-free assay will employ a mitochondrial AldDH2 produced recombinantly in *E. coli* cells.

In some embodiments, the in vitro cell-free assay will employ a fusion protein, comprising a mitochondrial AldDH2 fused in-frame to a fusion partner. In some embodiments, the fusion partner is an epitope tag. In some embodiments, the fusion partner is a metal chelating peptide. In some embodiments, the metal chelating peptide is a histidine multimer, e.g., $(His)_6$. In some embodiments, a $(His)_6$ multimer is fused to the amino terminus of the mitochondrial AldDH2; in other embodiments, a $(His)_6$ multimer is fused to the carboxyl terminus of the mitochondrial AldDH2. The $(His)_6$-mitochondrial AldDH2 fusion protein is purified using any of a variety of available nickel affinity columns (e.g. His-bind resin, Novagen).

In some embodiments, a test agent of interest is one that increases AldDH2 enzymatic activity by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, at least about 2-fold, at least about 5-fold, at least about 10-fold, at least about 20-fold, at least about 50-fold, or at least about 100-fold, or more, when compared to a control in the absence of the test agent.

In some embodiments, a test agent of interest is one that decreases AldDH2 enzymatic activity by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, at least about 2-fold, at least about 5-fold, at least about 10-fold, at least about 20-fold, at least about 50-fold, or at least about 100-fold, or more, when compared to a control in the absence of the test agent.

Identifying Agents that Modulate Mitochondrial AldDH2 mRNA and/or Polypeptide Levels In some embodiments, the invention provides methods for identifying agents that increase or decrease a level of AldDH2 mRNA and/or AldDH2 polypeptide. The methods generally involve contacting a cell that comprises a nucleic acid comprising a nucleotide sequence that encodes AldDH2; and determining the effect, if any, of the test agent on AldDH2 mRNA and/or polypeptide levels. In many embodiments, the assay is an in vitro, cell-based assay.

A candidate agent is assessed for any cytotoxic activity it may exhibit toward the cell used in the assay, using well-known assays, such as trypan blue dye exclusion, an MTT (3-(4,5-dimethylthiazol-2-yl)-2,5-diphenyl-2H-tetrazolium bromide) assay, and the like. Agents that do not exhibit cytotoxic activity are considered candidate agents.

A wide variety of cell-based assays may be used for identifying agents which increase or decrease a level of AldDH2 mRNA in a eukaryotic cell, using, for example, a eukaryotic that normally produces AldDH2 mRNA, a mammalian cell transformed with a construct comprising a AldDH2-encoding cDNA such that the cDNA is overexpressed, or, alternatively, a cell genetically modified with a construct comprising an AldDH2 promoter operably linked to a reporter gene. Where the assay is an in vitro cell-based assay, any of a variety of cells can be used.

The cells used in the assay are usually eukaryotic cells, including, but not limited to, rodent cells, human cells, and yeast cells. The cells may be primary cell cultures or may be immortalized cell lines. The cells may be "recombinant," e.g., the cell may have transiently or stably introduced therein a construct (e.g., a plasmid, a recombinant viral vector, or any other suitable vector) that comprises a nucleotide sequence encoding an AldDH2 polypeptide, or that comprises a nucleotide sequence that comprises an AldDH2 promoter operably linked to a reporter gene.

Accordingly, the present invention provides a method for identifying an agent, particularly a biologically active agent, that increases or decreases a level of AldDH2 expression in a cell, the method comprising: combining a candidate agent to be tested with a cell comprising a nucleic acid which encodes an AldDH2 polypeptide, or a construct comprising an AldDH2 promoter operably linked to a reporter gene; and determining the effect of said agent on AldDH2 expression.

An increase of at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, in the level (i.e., an amount) of AldDH2 mRNA and/or polypeptide following contacting the cell with a candidate agent being tested, compared to a control to which no agent is added, indicates that the agent increases AldDH2 expression.

A decrease of at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, in the level (i.e., an amount) of AldDH2 mRNA and/or polypeptide following contacting the cell with a candidate agent being tested, compared to a control to which no agent is added, indicates that the agent decreases AldDH2 expression.

AldDH2 mRNA and/or polypeptide whose levels are being measured can be encoded by an endogenous AldDH2 polynucleotide, or the AldDH2 polynucleotide encoding the AldDH2 mRNA and/or polypeptide can be one that is comprised within a recombinant vector and introduced into the cell, i.e., the AldDH2 mRNA and/or polypeptide can be encoded by an exogenous AldDH2 polynucleotide. For example, a recombinant vector may comprise a AldDH2 transcriptional regulatory sequence, such as a promoter sequence, operably linked to a AldDH2 coding region.

Alternatively, in some embodiments, a recombinant vector may comprise a AldDH2 transcriptional regulatory sequence operably linked to a reporter gene (e.g., β-galactosidase, chloramphenicol acetyl transferase, a fluorescent protein, luciferase, or other gene that can be easily assayed for expression), and the level of the reporter gene can be assayed. In these embodiments, the method for identifying an agent that modulates a level of AldDH2 expression in a cell, comprises: combining a candidate agent to be tested with a cell comprising a nucleic acid which comprises a AldDH2 gene transcriptional regulatory element operably linked to a reporter gene; and determining the effect of said agent on reporter gene expression.

A recombinant vector may comprise an isolated AldDH2 transcriptional regulatory sequence, such as a promoter sequence, operably linked to sequences coding for an AldDH2 polypeptide; or the transcriptional control sequences can be operably linked to coding sequences for an AldDH2 fusion protein comprising an AldDH2 polypeptide fused to a polypeptide which facilitates detection. In these embodiments, the method comprises combining a candidate agent to be tested with a cell comprising a nucleic acid which comprises an AldDH2 gene transcriptional regulatory element operably linked to an AldDH2 polypeptide-coding sequence; and determining the effect of said agent on AldDH2 expression, which determination can be carried out by measuring an amount of AldDH2 mRNA, AldDH2 polypeptide, or AldDH2 fusion polypeptide produced by the cell.

Cell-based assays generally comprise the steps of contacting the cell with an agent to be tested, forming a test sample, and, after a suitable time, assessing the effect of the agent on AldDH2 expression. A control sample comprises the same cell without the candidate agent added. AldDH2 expression levels are measured in both the test sample and the control sample. A comparison is made between AldDH2 expression level in the test sample and the control sample. AldDH2 expression can be assessed using conventional assays. For example, when a mammalian cell line is transformed with a construct that results in expression of AldDH2, AldDH2 mRNA levels can be detected and measured, or AldDH2 polypeptide levels can be detected and measured. A suitable period of time for contacting the agent with the cell can be determined empirically, and is generally a time sufficient to allow entry of the agent into the cell and to allow the agent to have a measurable effect on AldDH2 mRNA and/or polypeptide levels. Generally, a suitable time is between 10 minutes and 24 hours, or from about 1 hour to about 8 hours.

Detecting AldDH2 mRNA Levels

Methods of measuring AldDH2 mRNA levels are known in the art, and any of these methods can be used in the methods of the present invention to identify an agent which modulates AldDH2 mRNA level in a cell, including, but not limited to, a polymerase chain reaction (PCR), such as a PCR employing detectably labeled oligonucleotide primers, and any of a variety of hybridization assays. The AldDH2 mRNA may be assayed directly or reverse transcribed into cDNA for analysis. The mRNA may be purified, but need not be. The mRNA is in some embodiments isolated from the cell. In other embodiments, quantitation is performed on a cell lysate.

AldDH2 mRNA may be amplified by conventional techniques, such as a PCR method, to provide sufficient amounts for analysis. The use of PCR is described in Saiki, et al. (1985), *Science* 239: 487, and a review of techniques may be found in Sambrook, et al. *Molecular Cloning: A Laboratory Manual*, CSH Press 1989, pp. 14.2-14.33. Quantitative PCR techniques are amply described in the literature, and are suitable for use in a subject method. See, e.g., *Quantitative PCR Protocols* (Methods in Molecular Medicine, Vol. 26), B. Kochanowski and U. Reischl, eds., (1999) Humana Press; and *The PCR Technique: Quantitative PCR* (BioTechniques Update series), J. W. Larrick, ed. (1997) Eaton Publ. Co.

A detectable label may be included in an amplification reaction, e.g., a PCR reaction. Suitable labels include fluorochromes, e.g. fluorescein isothiocyanate (FITC), rhodamine, TEXAS RED, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The following is an exemplary, non-limiting example of a PCR reaction that would be suitable for use in a subject method. A PCR reaction mixture is set up that contains the following components: DNA 100 ng; 10X Buffer (100 mM Tris, pH 8.3; 500 mM KCl) 5 µl; 25 mM dNTPs 4 µl; 25 mM $MgCl_2$ 3 µl; Forward Primer (10 µM) 2 µl; Reverse Primer (10 µM) 2 µl; Taq polymerase (5U/l) 0.2 µl; volume total 50 µl. Suitable PCR parameters are as follows: 95° C. 3 minutes to denature the template; followed by 35 cycles of: 94° C. 1 minute; 55° C. 1 minute; and 72° C. 1.5 minute. Following the 35 cycles, the reaction is carried out further at 72° C. 10 minutes. Those skilled in the art can readily determine other suitable PCR components and conditions.

A variety of other methods for determining the nucleic acid abundance in a sample are known to those of skill in the art, where particular methods of interest include those described in: Pietu et al., Genome Res. (June 1996) 6: 492-503; Zhao et al., Gene (Apr. 24, 1995) 156: 207-213; Soares, Curr. Opin.

Biotechnol. (October 1997) 8: 542-546; Raval, J. Pharmacol Toxicol Methods (November 1994) 32: 125-127; Chalifour et al., Anal. Biochem (Feb. 1, 1994) 216: 299-304; Stolz & Tuan, Mol. Biotechnol. (December 19960 6: 225-230; Hong et al., Bioscience Reports (1982) 2: 907; and McGraw, Anal. Biochem. (1984) 143: 298. Also of interest are the methods disclosed in WO 97/27317, the disclosure of which is herein incorporated by reference.

Detecting AldDH2 Polypeptide Levels

Similarly, AldDH2 polypeptide levels can be measured using any standard method, several of which have been described herein, including, but not limited to, an immunoassay such as an enzyme-linked immunosorbent assay (ELISA), for example an ELISA employing a detectably labeled antibody specific for a mitochondrial AldDH2 polypeptide.

AldDH2 polypeptide levels can also be measured in cells harboring a recombinant construct comprising a nucleotide sequence that encodes an AldDH2 fusion protein, where the fusion partner provides for a detectable signal or can otherwise be detected. For example, where the fusion partner provides an immunologically recognizable epitope (an "epitope tag"), an antibody specific for an epitope of the fusion partner can be used to detect and quantitate the level of AldDH2. In some embodiments, the fusion partner provides for a detectable signal, and in these embodiments, the detection method is chosen based on the type of signal generated by the fusion partner. For example, where the fusion partner is a fluorescent protein, fluorescence is measured. Fluorescent proteins include, but are not limited to, a green fluorescent protein (GFP), including, but not limited to, a "humanized" version of a GFP, e.g., wherein codons of the naturally-occurring nucleotide sequence are changed to more closely match human codon bias; a GFP derived from *Aequoria victoria* or a derivative thereof, e.g., a "humanized" derivative such as Enhanced GFP, which are available commercially, e.g., from Clontech, Inc.; a GFP from another species such as *Renilla reniformis, Renilla mulleri,* or *Ptilosarcus guernyi*, as described in, e.g., WO 99/49019 and Peelle et al. (2001) *J. Protein Chem.* 20: 507-519; "humanized" recombinant GFP (hrGFP) (Stratagene); any of a variety of fluorescent and colored proteins from Anthozoan species, as described in, e.g., Matz et al. (1999) *Nature Biotechnol.* 17: 969-973; and the like. Where the fusion partner is an enzyme that yields a detectable product, the product can be detected using an appropriate means, e.g., β-galactosidase can, depending on the substrate, yield colored product, which is detected spectrophotometrically, or a fluorescent product; luciferase can yield a luminescent product detectable with a luminometer; etc.

A number of methods are available for determining the level of a protein in a particular sample. For example, detection may utilize staining of cells or histological sections with labeled antibodies, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. Alternatively, the secondary antibody conjugated to a fluorescent compound, e.g. fluorescein, rhodamine, Texas red, etc. The absence or presence of antibody binding may be determined by various methods, including flow cytometry of dissociated cells, microscopy, radiography, scintillation counting, etc.

Agents

The present invention further provides active agents that increase a level and/or activity of mitochondrial AldDH2 in a cell of an individual. The agents are useful for treating ischemia in an individual; and for reducing ischemic tissue damage in an organ. The present invention further provides compositions, including pharmaceutical compositions, comprising a subject agent.

In some embodiments, an "active" agent is an agent that increases a level and/or activity of AldDH2, and that is effective to reduce ischemic tissue damage by at least about 10%, at least about 15%, at least about 20%, at least about 25%, at least about 30%, at least about 40%, or at least about 50% when compared to the level of damage in the absence of the active agent.

In other embodiments, an "active" agent is an agent that decreases a level and/or activity of AldDH2, and that is effective to increase ischemic tissue damage by at least about 10%, at least about 15%, at least about 20%, at least about 25%, at least about 30%, at least about 40%, or at least about 50% when compared to the level of damage in the absence of the active agent.

In many embodiments, the agent is a small molecule, e.g., a small organic or inorganic compound having a molecular weight of more than 50 and less than about 10,000 daltons. Agents may comprise functional groups necessary for structural interaction with proteins, particularly hydrogen bonding, and may include at least an amine, carbonyl, hydroxyl or carboxyl group, and may contain at least two of the functional chemical groups. The agents may comprise cyclical carbon or heterocyclic structures and/or aromatic or polyaromatic structures substituted with one or more of the above functional groups. Agents are also found among biomolecules including peptides, saccharides, fatty acids, steroids, purines, pyriridines, derivatives, structural analogs or combinations thereof.

In some embodiments, an active agent that decreases a level or activity of AldDH2 is a dominant negative mutant of AldDH2; an intrabody; a peptide aptamer; an antisense that reduces a level of AldDH2; a ribozyme that reduces a level of AldDH2; an siRNA that reduces the level of AldDH2; and the like.

Peptide aptamers are peptides or small polypeptides that act as dominant inhibitors of protein function. Peptide aptamers specifically bind to target proteins, blocking their function ability. Kolonin and Finley, PNAS (1998) 95: 14266-14271. Due to the highly selective nature of peptide aptamers, they may be used not only to target a specific protein, but also to target specific functions of a given protein (e.g. a signaling function). Further, peptide aptamers may be expressed in a controlled fashion by use of promoters which regulate expression in a temporal, spatial or inducible manner. Peptide aptamers act dominantly; therefore, they can be used to analyze proteins for which loss-of-function mutants are not available.

Peptide aptamers that bind with high affinity and specificity to a target protein may be isolated by a variety of techniques known in the art. Peptide aptamers can be isolated from random peptide libraries by yeast two-hybrid screens (Xu et al., PNAS (1997) 94: 12473-12478). They can also be isolated from phage libraries (Hoogenboom et al., Immunotechnology (1998) 4: 1-20) or chemically generated peptides/libraries.

Intracellularly expressed antibodies, or intrabodies, are single-chain antibody molecules designed to specifically bind and inactivate target molecules inside cells. Intrabodies have been used in cell assays and in whole organisms. Chen et al., Hum. Gen. Ther: (1994) 5: 595-601; Hassanzadeh et al., Febs Lett. (1998) 16(1,2): 75-80 and 81-86. Inducible expression vectors can be constructed with intrabodies that react specifically with AldDH2 protein.

In some embodiments, the active agent is an agent that modulates, and generally decreases or down regulates, the expression of the gene encoding AldDH2 in the host. Such agents include, but are not limited to, antisense RNA, interfering RNA (including short interfering RNA; "siRNA"), ribozymes, and the like.

In some embodiments, the active agent is an interfering RNA (RNAi). RNAi includes double-stranded RNA interference (dsRNAi). Use of RNAi to reduce a level of a particular mRNA and/or protein is based on the interfering properties of double-stranded RNA derived from the coding regions of gene. In one example of this method, complementary sense and antisense RNAs derived from a substantial portion of the AldDH2 gene are synthesized in vitro. The resulting sense and antisense RNAs are annealed in an injection buffer, and the double-stranded RNA injected or otherwise introduced into the subject (such as in their food or by soaking in the buffer containing the RNA). See, e.g., WO99/32619. In another embodiment, dsRNA derived from an AldDH2 gene is generated in vivo by simultaneous expression of both sense and antisense RNA from appropriately positioned promoters operably linked to AldDH2 coding sequences in both sense and antisense orientations.

One approach well known in the art is short interfering RNA (siRNA) mediated gene silencing where expression products of an AldDH2 gene are targeted by specific double stranded AldDH2-derived siRNA nucleotide sequences that are complementary to at least a 19-25 nt long segment (e.g., a 20-21 nucleotide sequence) of the AldDH2 gene transcript, including the 5' untranslated (UT) region, the ORF, or the 3' UT region. In some embodiments, short interfering RNAs are about 19-25 nt in length. See, e.g., PCT applications WO0/44895, WO99/32619, WO01/75164, WO01/92513, WO01/29058, WO01/89304, WO02/16620, and WO02/29858 for descriptions of siRNA technology.

Antisense molecules can be used to down-regulate expression of the gene encoding AldDH2 in cells. Antisense compounds include ribozymes, external guide sequence (EGS) oligonucleotides (oligozymes), and other short catalytic RNAs or catalytic oligonucleotides which hybridize to the target nucleic acid and modulate its expression.

The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), Nature Biotechnol. 14: 840-844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1996), supra.) Preferred oligonucleotides are chemically modified from the native phosphodiester structure, in order to increase their intracellular stability and binding affinity. A number of such modifications have been described in the literature, which modifications alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The β-anomer of deoxyribose may be used, where the base is inverted with respect to the natural α-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Exemplary modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Oligonucleotides having a morpholino backbone structure (Summerton, J. E. and Weller D. D., U.S. Pat. No. 5,034,506)

or a peptide nucleic acid (PNA) backbone (P. E. Nielson, M. Egholm, R. H. Berg, O. Buchardt, Science 1991, 254: 1497) can also be used. Morpholino antisense oligonucleotides are amply described in the literature. See, e.g., Partridge et al. (1996) *Antisense Nucl. Acid Drug Dev.* 6: 169-175; and Summerton (1999) *Biochem. Biophys. Acta* 1489: 141-158.

Anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res.* 23: 4434-42). Examples of oligonucleotides with catalytic activity are described in WO 9506764. Conjugates of anti-sense oligodeoxynucleotides with a metal complex, e.g. terpyridylCu(II), capable of mediating mRNA hydrolysis are described in Bashkin et al. (1995), *Appl. Biochem. Biotechnol.* 54: 43-56.

In some embodiments, a subject agent is formulated with one or more pharmaceutically acceptable excipients. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Formulations, Dosages, and Routes of Administration

The invention provides formulations, including pharmaceutical formulations, comprising an active agent that increases or decreases a level and/or an activity of mitochondrial AldDH2. In general, a formulation comprises an effective amount of an agent that increases or decreases a level and/or an activity of AldDH2. In some embodiments, an "effective amount" means a dosage sufficient to produce a desired result, e.g., an increase in a level and/or an activity of AldDH2, a reduction in ischemic tissue damage, an increase in organ function. In many embodiments, the desired result is at least an increase in a level and/or an activity of AldDH2 as compared to a control. In other embodiments, an "effective amount" means a dosage sufficient to produce a desired result, e.g., a decrease in a level and/or an activity of AldDH2, a reduction in solid tumor growth, a reduction in solid tumor mass, etc. In many embodiments, the desired result is at least a decrease in a level and/or an activity of AldDH2 as compared to a control.

Formulations

In the subject methods, the active agent(s) may be administered to the host using any convenient means capable of resulting in the desired increase or decrease in a level and/or an activity of AldDH2. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

An active agent can be administered sublingually, where the agent is formulated in a manner suitable for sublingual administration, e.g., in a tablet, capsule, dissolvable strip, and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Other modes of administration will also find use with the subject invention. For instance, an agent of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

An agent of the invention can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

In some embodiments, a subject agent is delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present invention. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, the present methods of drug delivery can be accomplished using any of a variety of refillable, pump systems. Pumps provide consistent, controlled release over time. Typically, the agent is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to a subdermal, subcutaneous, intramuscular, or other suitable site within a subject's body. Subcutaneous implantation sites are generally preferred because of convenience in implantation and removal of the drug delivery device.

Drug release devices suitable for use in the invention may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present invention. Examples of such devices include those described in, for example, U.S. Pat. Nos. 4,692,147; 4,360,019; 4,487,603; 4,360,019; 4,725,852; and the like. In general, the present methods of drug delivery can be accomplished using any of a variety of refillable, non-exchangeable pump systems. Pumps and other convective systems are generally preferred due to their generally more consistent, controlled release over time. Osmotic pumps are particularly preferred due to their combined advantages of more consistent controlled release and relatively small size (see, e.g., PCT published application no. WO 97/27840 and U.S. Pat. Nos. 5,985,305 and 5,728,396)). Exemplary osmotically-driven devices suitable for use in the invention include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted infra, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, a subject agent is delivered using an implantable drug delivery system, e.g., a system that is programmable to provide for administration of the agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present invention is the Synchromed infusion pump (Medtronic).

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosages

Although the dosage used will vary depending on the clinical goals to be achieved, a suitable dosage range is one which provides up to about 1 µg to about 1,000 µg or about 10,000 µg of an agent that increases or decreases a level and/or an activity of AldDH2 can be administered in a single dose. Alternatively, a target dosage of an agent that increases or decreases a level and/or an activity of AldDH2 can be considered to be about in the range of about 0.1-1000 µM, about 0.5-500 µM, about 1-100 µM, or about 5-50 µM in a sample of host blood drawn within the first 24-48 hours after administration of the agent.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

Routes of Administration

An agent that increases or decreases a level and/or an activity of AldDH2 is administered to an individual using any available method and route suitable for drug delivery, including in vivo and ex vivo methods, as well as systemic and localized routes of administration.

Conventional and pharmaceutically acceptable routes of administration include intranasal, intratumoral, intramuscular, intratracheal, subcutaneous, sublingual, intradermal, topical application, intravenous, rectal, nasal, oral and other enteral and parenteral routes of administration. Routes of administration may be combined, if desired, or adjusted depending upon the agent and/or the desired effect. The composition can be administered in a single dose or in multiple doses.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intratumoral, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral and rectal (e.g., using a suppository) delivery.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as reperfusion injury. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

Ex vivo administration is also contemplated, e.g., where an organ is removed from an individual and is subsequently introduced into the same individual or a different individual. For example, an organ can be placed in a medium that contains a subject agent.

A variety of hosts (wherein the term "host" is used interchangeably herein with the terms "subject" and "patient") are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of the active agent, e.g. in oral or injectable doses, are provided. In such kits, in addition to the containers containing the unit doses will be an informational package insert describing the use and attendant benefits of the drugs in treating pathological condition of interest. Preferred compounds and unit doses are those described herein above.

Treatment Methods

The present invention provides methods for treating disorders amenable to treatment by increasing a level and/or activity of AldDH2. The present invention provides methods for treating disorders amenable to treatment by decreasing a level and/or activity of AldDH2.

Increasing a Level and/or Activity of AldDH2

The present invention provides methods for treating ischemia, including prophylactic methods, in an individual, the methods generally involving administering to an individual in need thereof an effective amount of an agent that increases a level and/or activity of a mitochondrial AldDH2 in the individual. Ischemic conditions that are amenable to treatment with a subject method include ischemia that result from any condition or event, including, but not limited to, myocardial infarct, cardiac surgery, brain trauma, cerebrovascular disease, stroke, spinal cord injury, subarachnoid hemorrhage, other major surgery in which ischemia to variety of organs occur, organ transplantation and the like.

The present invention provides methods for treating chronic free-radical associated diseases in an individual, the methods generally involving administering to an individual in need thereof an effective amount of an agent that increases a level and/or activity of a mitochondrial AldDH2 in the individual. Free radical-associated disorders that are amenable to treatment with a subject method include neurodegenerative diseases such as Parkinson's disease, Alzheimer's disease, amyotropic lateral sclerosis, and the like. In many embodiments, a free radical-associated disease is treated by chronic (e.g., daily) treatment with an agent that increases a level and/or activity of AldDH2.

In some embodiments, the agent is administered before a predicted or anticipated ischemic event, e.g., from about 1 hour to about 1 week before the ischemic event, e.g., from about 1 hour to about 2 hours, from about 2 hours to about 4 hours, from about 4 hours to about 8 hours, from about 8 hours to about 12 hours, from about 12 hours to about 16 hours, from about 16 hours to about 24 hours, from about 24 hours to about 36 hours, from about 36 hours to about 48 hours, from about 48 hours to about 72 hours, or from about 72 hours to about 1 week preceding the ischemic event.

Pretreatment with an active agent is desirable under certain circumstances, for example, when a subject has already experienced a stroke, when a subject is about to undergo cardiac surgery, etc. For example, a patient who has already experienced a stroke will have an increased probability of experiencing a second stroke. Subjects who are susceptible to transient ischemic attacks also have an increased risk of a stroke.

Subjects who suffer a subarachnoid hemorrhage may experience further ischemic events induced by vasospasms that constrict the blood vessels. Subjects who experience trauma to organs such as the brain are also susceptible to an ischemic event. Subjects undergoing surgery over an extended period of time are also susceptible to an ischemic event. The above situations exemplify circumstances when a subject would benefit from pretreatment.

In some embodiments, an active agent is administered after an ischemic event. For example, an active agent is effective in reducing the adverse effects of an ischemic event such as cardiac ischemia, reperfusion injury, cerebrovascular disease, subarachnoid hemorrhage, and trauma. In some embodiments, an active agent is administered within 1 minute to within 15 hours, e.g., from about 1 minute to about 5 minutes, from about 5 minutes to about 10 minutes, from about 10 minutes to about 15 minutes, from about 15 minutes to about 30 minutes, from about 30 minutes to about 60 minutes, from about 60 minutes to about 2 hours, from about 2 hours to about 4 hours, from about 4 hours to about 8 hours, from about 8 hours to about 12 hours, or from about 12 hours to about 15 hours, following the ischemic event. In some embodiments, an increased concentration of the active agent is maintained in the plasma for at least several hours to several days following the ischemic event.

Decreasing a Level and/or Activity of AldDH2

The present invention provides methods for increasing the susceptibility of a solid tumor to ischemic damage by decreasing the level and/or activity of AldDH2. The methods generally involve administering to an individual having a solid tumor an effective amount of an agent that reduces a level and/or activity of AldDH2.

In some embodiments, an agent that decreases a level and/or activity of AldDH2 is administered as adjuvant therapy to a standard cancer therapy. Standard cancer therapies include surgery (e.g., surgical removal of cancerous tissue), radiation therapy, bone marrow transplantation, chemotherapeutic treatment, biological response modifier treatment, and certain combinations of the foregoing.

Radiation therapy includes, but is not limited to, x-rays or gamma rays that are delivered from either an externally applied source such as a beam, or by implantation of small radioactive sources.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g anthracycline, daunorubicin hydrochloride (daunomycin, rubidomycin, cerubidine), idarubicin, doxorubicin, epirubicin and morpholino derivatives, etc.; phenoxizone biscyclopeptides, e.g dactinomycin; basic glycopeptides, e.g bleomycin; anthraquinone glycosides, e.g plicamycin (mithramycin); anthracenediones, e.g mitoxantrone; aziridinopyrrolo indolediones, e.g mitomycin; macrocyclic immunosuppressants, e.g cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Biological response modifiers suitable for use in connection with the methods of the invention include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) IFN-α; (7) IFN-γ; (8) colony-stimulating factors; (9) inhibitors of angiogenesis; and (10) antagonists of tumor necrosis factor.

A subject method is effective to reduce a tumor load by at least about 5%, at least about 10%, at least about 20%, at least about 25%, at least about 50%, at least about 75%, at least about 85%, or at least about 90%, up to total eradication of the tumor, when compared to a suitable control. Thus, in these embodiments, an "effective amount" of an agent that decreases a level and/or activity of AldDH2 is an amount sufficient to reduce a tumor load by at least about 5%, at least about 10%, at least about 20%, at least about 25%, at least about 50%, at least about 75%, at least about 85%, or at least about 90%, up to total eradication of the tumor, when compared to a suitable control. In an experimental animal system, a suitable control may be a genetically identical animal not treated with the agent. In non-experimental systems, a suitable control may be the tumor load present before administering the agent. Other suitable controls may be a placebo control.

Whether a tumor load has been decreased can be determined using any known method, including, but not limited to, measuring solid tumor mass; counting the number of tumor cells using cytological assays; fluorescence-activated cell sorting (e.g., using antibody specific for a tumor-associated antigen); computed tomography scanning, magnetic resonance imaging, and/or x-ray imaging of the tumor to estimate and/or monitor tumor size; measuring the amount of tumor-associated antigen in a biological sample, e.g., blood; and the like.

Subjects Suitable for Treatment

Subjects suitable for treatment with a subject agent and/or a subject method, where the agent increases a level and/or activity of AldDH2, include individuals who are scheduled to undergo cardiac surgery or who have undergone cardiac surgery; individuals who have experienced a stroke; individuals who have suffered brain trauma; individuals who have prolonged surgery; and individuals who will be subjected to organ transplantation.

Subjects suitable for treatment with a subject agent and/or a subject method, where the agent decreases a level and/or activity of AldDH2, include individuals having a solid tumor. Solid tumors include, but are not limited to, histiocytic lymphoma, cancers of the brain, genitourinary tract, lymphatic system, stomach, larynx and lung, including lung adenocarcinoma and small cell lung cancer.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s, second(s); min, minute(s); hr, hour(s); and the like.

Example 1

Ex vivo Langendorff preparation of rat hearts were used as a model to assess the damage incurred by no-flow ischemia and reperfusion injury. This is an experimental model that mimics the clinical situation of myocardial infarction in patients. Rat hearts were excised and cannulated on a Langendorff apparatus via the aorta. Retrograde perfusion was carried out using the standard oxygenated Kreb-Hensleit buffer maintained at 37° C. All hearts were stabilized by an initial 5- to 10-minute perfusion period followed by delivery of different cardioprotective agents or AldDH2 inhibitors for 10-30 minutes, depending on the reagent. Reagents used in some of the representative experiments including ethanol (50 mM), εPKC isozyme-selective activator and inhibitor peptides (1 μM), cyanamide (5 mM) and nitroglycerin (2 EM). Ischemia was then introduced by 25 minutes of no-flow followed by 60 minutes of reperfusion.

The degree of ischemia/reperfusion damage was measured by two independent commonly accepted parameters. In one assay, a cross-section of heart slices were obtained immediately after reperfusion and stained with 2,3,5-triphenyl-tetrazolium chloride (TTC) for infarct size measurement. In another assay, creatine phosphate kinase activity was measured from reperfusate of each heart collected during reperfusion. The data indicated that the two methods yielded comparable results for the assessment of cardiac damage. Homogenates from each heart was also obtained from a separate section of the identical sample and analyzed for aldehyde dehydrogenase enzymatic activity. Enzymatic activity was determined by a standard spectrophotometric method described above using acetaldehyde as the substrate and $NAD^+$ as a cofactor. The results are shown in FIGS. 1-8.

FIG. 1: Ethanol metabolism in the liver and the role of AldDH2 in the process. In the liver, ethanol is metabolized to acetic acid by a two-step oxidative enzymatic pathway. In the first step, ethanol is oxidized to acetaldehyde using alcohol dehydrogenase. Acetaldehyde is further oxidized to acetic acid by aldehyde dehydrogenase. In both steps, NADH is generated using NAD as the electron acceptor. Pyrazole, disulfiram and cyanamide are three of the known pharmacological drugs used to inhibit the enzymes involved in this pathway. Pyrazole is an inhibitor of alcohol dehydrogenase, whereas disulfiram and cyanamide are inhibitors for the cytosolic form (AldDH1) and mitochondrial form (AldDH2) of aldehyde dehydrogenases, respectively.

Figure 2:
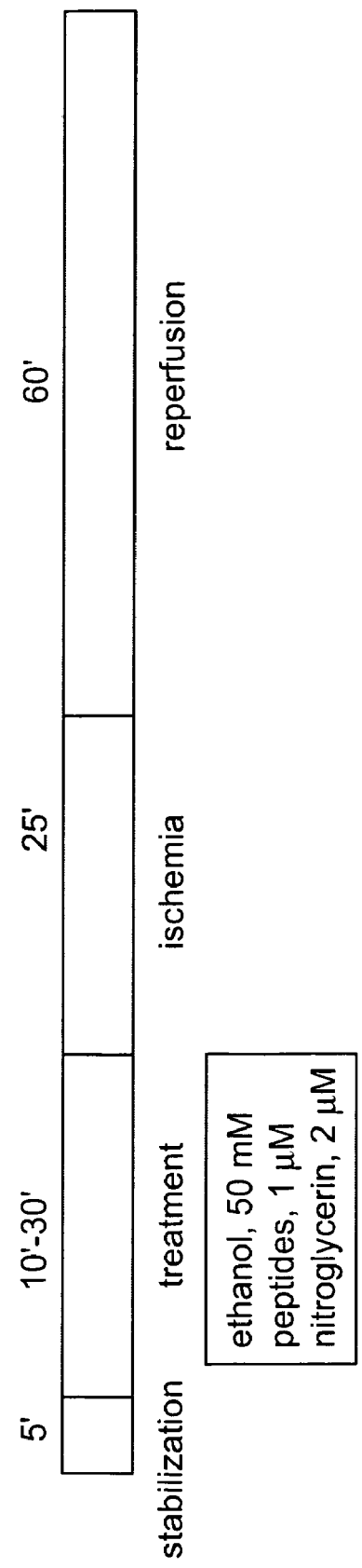
FIG. 2 depicts an experimental protocol using an ex vivo Langendorff heart.

FIG. 2: An experimental protocol using an ex vivo Langendorff heart. Rat hearts were excised and cannulated on a Langendorff apparatus via aorta. Retrograde perfusion was carried out using the standard oxygenated Kreb-Hensleit buffer maintained at 37° C. All hearts were stabilized by an initial 5 to 10-minute perfusion period followed by delivery of different cardioprotective agents or AldHD2 inhibitors for 10-30 minutes, depending on the reagents. Treatments included ethanol (50 mM); peptides (1 µM); or nitroglycerin (2 µM). Peptides used were a selective activator (εV1-7) or inhibitor (εV1-2) or epsilon protein kinase C (εPKC). Ischemia was then introduced by 25 minutes of no-flow followed by 60 minutes of reperfusion. Sections of each heart were finally obtained for infarct size determination by 2,3,5-triphenyl-tetrazolium chloride (TTC) staining and aldehyde dehydrogenase enzyme activity assay using acetaldehyde as a substrate.

Figure 3:
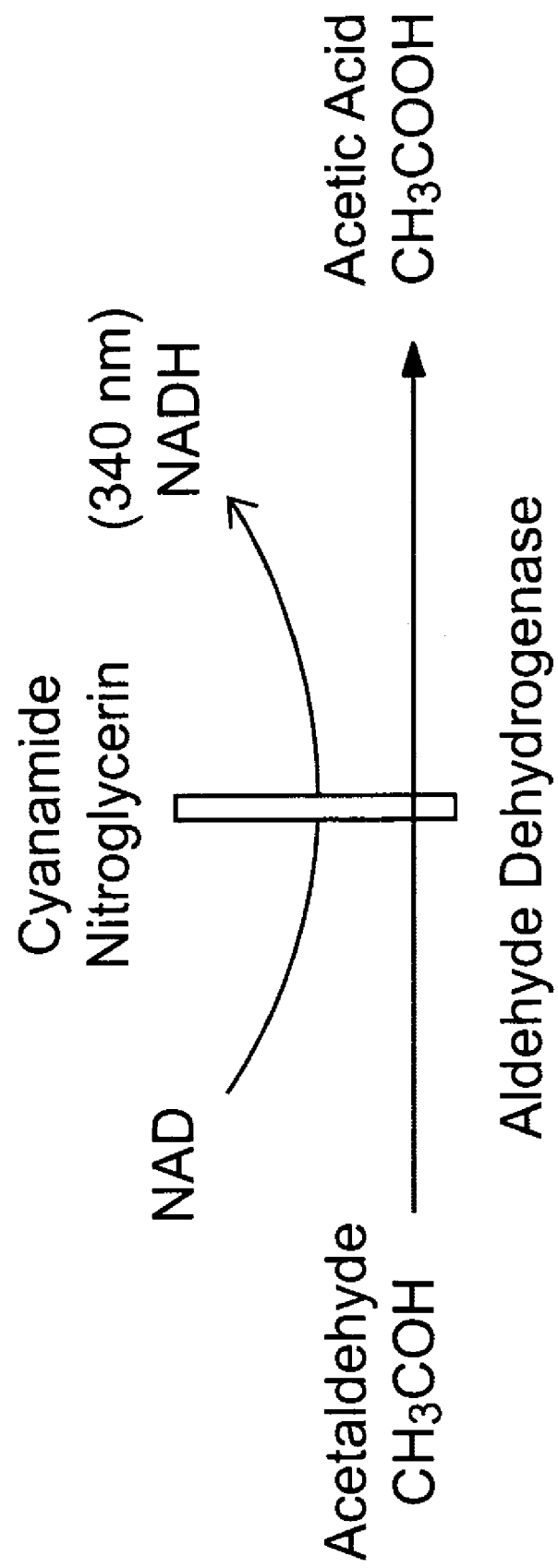
FIG. 3 depicts formation of acetic acid from acetaldehyde by action of aldehyde dehydrogenase.

FIG. 3: Formation of acetic acid from acetaldehyde by action of aldehyde dehydrogenase. Enzymatic activity of aldehyde dehydrogenase is determined by a standard photospectrometric method using acetaldehyde as a substrate. In this reaction, aldehyde dehydrogenase catalyzes the oxidation of acetaldehyde to acetic acid. Concomitantly, $NAD^+$ is reduced to NADH resulting in an increase in absorbance at 340 nm wavelength in a photospectrometer. The rate of NADH increase is proportional to the enzymatic activity of aldehyde dehydrogenase. A reduction of NADH accumulation and therefore absorbance at 340 nm is expected in heart samples treated with aldehyde dehydrogenase inhibitors such as cyanamide or nitroglycerin.

Figure 4:
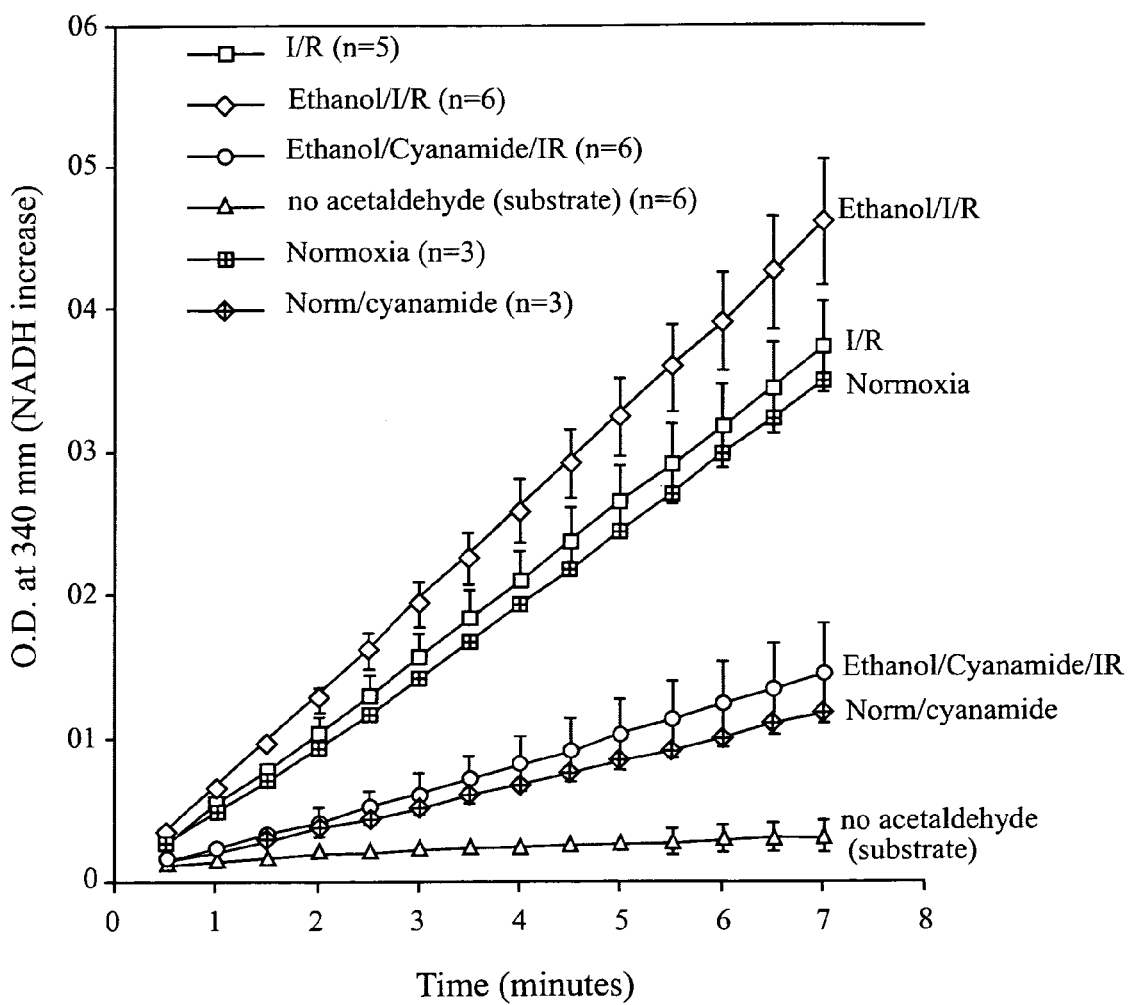
FIG. 4 is a graph depicting an ALDH activity assay.

FIG. 4: ALDH activity assay. An example of aldehyde dehydrogenase activity assay as measured by the increase of NADH at 340 nm absorbance. Pretreatment of a cardioprotective agent, ethanol, before ischemia leads to an increase in the rate of absorbance as compared to ischemia/reperfusion (I/R) alone or normoxia. On the contrary, treatment with an aldehyde dehydrogenase inhibitor, cyanamide leads to a reduction of NADH accumulation in both ethanol treated ischemic samples or normoxic (Norm) heart samples.

Figure 5:
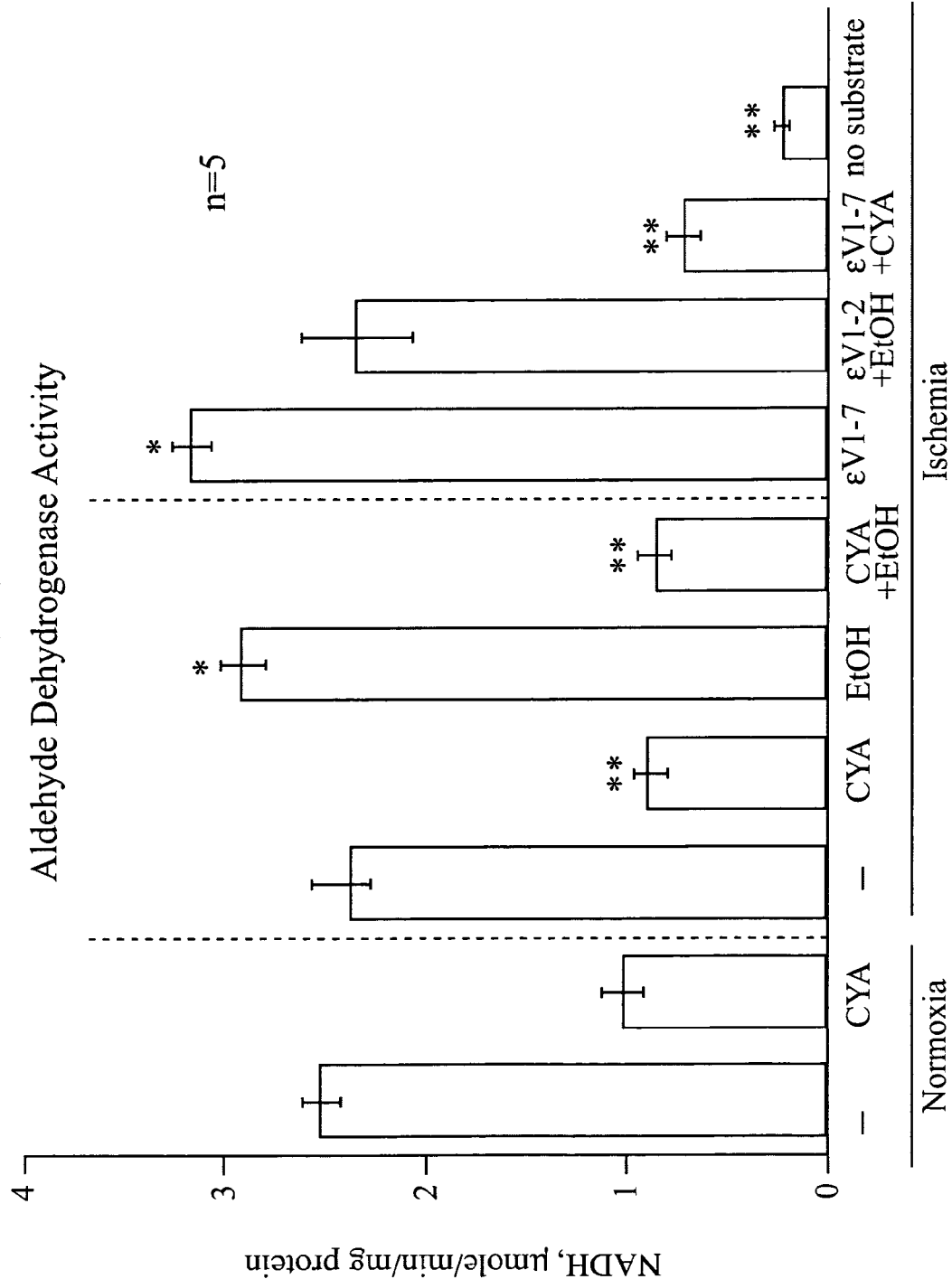
FIG. 5 is a graph depicting the effect of ethanol and εPKC on AldDH2 activity.

FIG. 5: Ethanol and εPKC activation increase AldDH2 activity. Induction of AldDH2 activity is observed by treatment of two cardioprotective agents, ethanol and εPKC agonist peptide (εV1-7). Acute treatment of 50 mM ethanol for 10 minutes resulted in a 25% increase in AldHD2 activity (*$p<0.05$), and treatment of 1 µM of εPKC agonist peptide, eV1-7 resulted in a 34% increase in AldHD2 activity (*$p<0.05$) as compared to ischemia/reperfusion control. The effect of ethanol induction is inhibited by treatment of an εPKC antagonist peptide, εV1-2. In addition, the effect of induction is also greatly abolished in the presence of an effective AldHD2 inhibitor, cyanamide. Cyanamide treatment in the absence or presence of ethanol or peptide dramatically inhibits AldDH2 by 63%, 64% and 74% respectively (**$p<0.01$) during ischemia reperfusion. In normoxic heart samples, inhibition of AldDH2 activity by cyanamide is also observed. εV1-2, εPKC-selective inhibitor; εV1-7, εPKC-selective activator; EtOH, ethanol; CYA, cyanamide.

The effect of cyanamide on cardioprotection from ischemia was explored. It was shown that AldDh2 activity is essential for cardioprotection from ischemia and reperfusion-induced damage. Ischemic damage was determined by TTC staining of heart sections. Compared to an ischemia/reperfusion control heart, pretreatment of ethanol leads to cardioprotection via an εPKC-mediated signaling pathway. Inhibition of AldDH2 by cyanamide eliminates the protective effect of ethanol and leads to an even greater damage as compared to control. Under normoxic condition, AldDH2 is not required since the cyanamide treated heart does not produce any significantly greater damage than the control heart.

Figure 6:
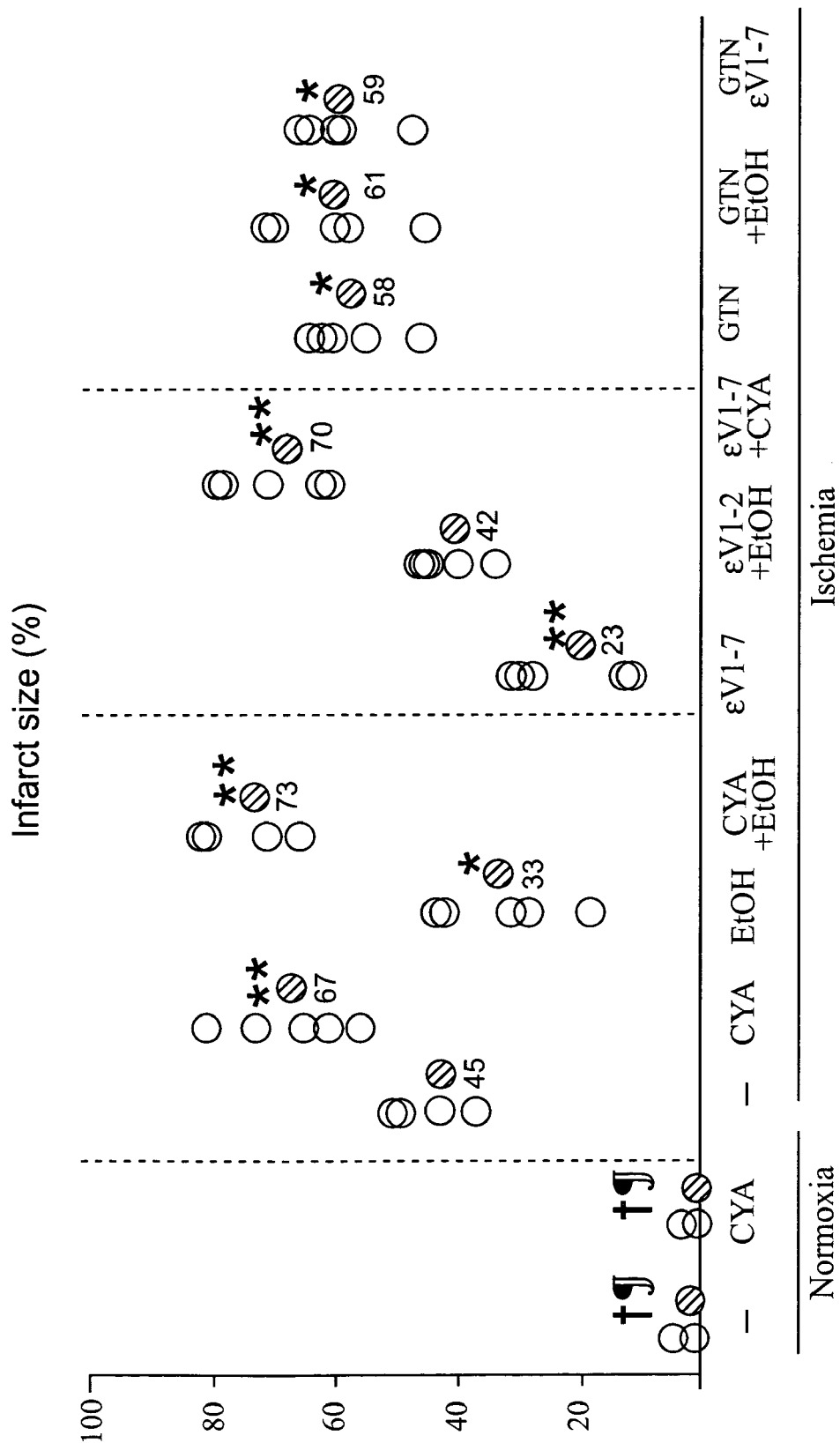
FIG. 6 depicts the effect of cyanamide and nitroglycerine (GTN) on cardioprotection from ischemia.

FIG. 6: AldDH2 activity is essential for cardioprotection from ischemia and reperfusion-induced damage; effect of cyanamide and nitroglycerine. Nitroglycerine is metabolized by AldDh2, and prolonged incubation with nitroglycerine inhibits AldDH2 activity. It was reasoned that if AldDH2 activity is required for cardioprotection, that prolonged exposure to nitroglycerine will cause a decrease in AldDh2 activity and will reduce protection by ethanol and εPKC activation. Compared to no treatment control, inhibition of AldDH2 by cyanamide leads to a 49% increase in ischemia/reperfusion damage as measured by infarct size ($p<0.01$). In samples treated with cardioprotective agents, ethanol or εPKC agonist peptide, cyanamide also leads to a greater degree of infarct damage with an increase of 62% and 56% respectively ($p<0.01$). Desensitization of AldDH2 by nitroglycerin also resulted in an increase in infarct size. Nitroglycerin treatment alone shows an increase of 29% in infarct size as compare to control (*$p<0.05$). Nitroglycerin treatment in the presence of ethanol and εPKC agonist peptide results in increased damage by 36% and 31% respectively (*$p<0.05$).

Figure 7:
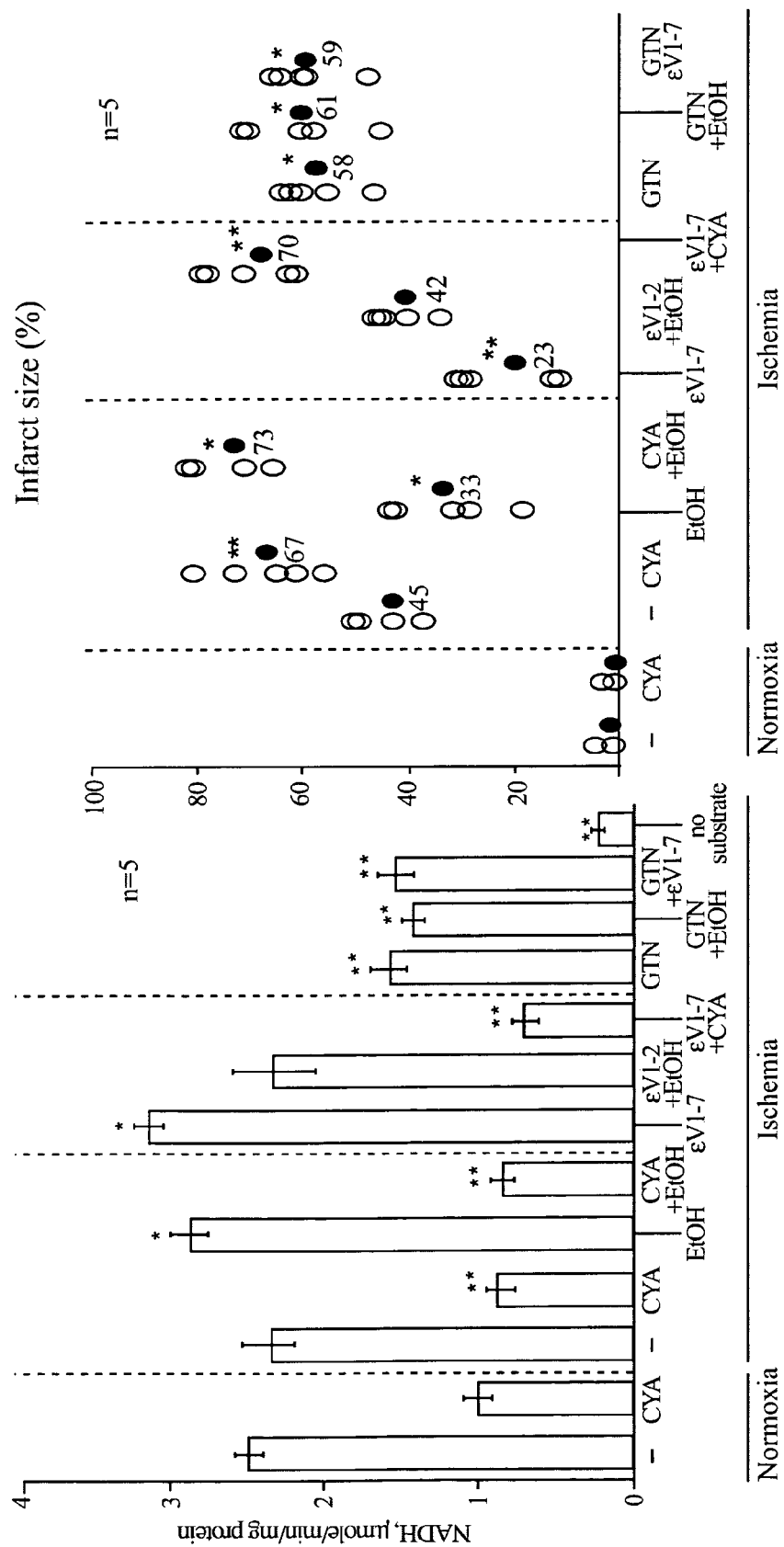
FIG. 7 depicts the inverse correlation between AldDH2 activity and infarct size.

FIG. 7: Inverse correlation between AldDH2 activity and infarct size. Data from FIG. 6 (and the I/R heart data described above) indicates an inverse correlation between AldDH2 activity and infarct size during ischemia/reperfusion. Induction of AldDH2 activity invariably leads to a smaller infarct size and reduced AldDH2 activity leads to greater infarct damage. The only exception observed is in the normoxic condition, which indicates that AldDH2 activity is not essential under normal non-stressed physiological condition.

Figure 8:
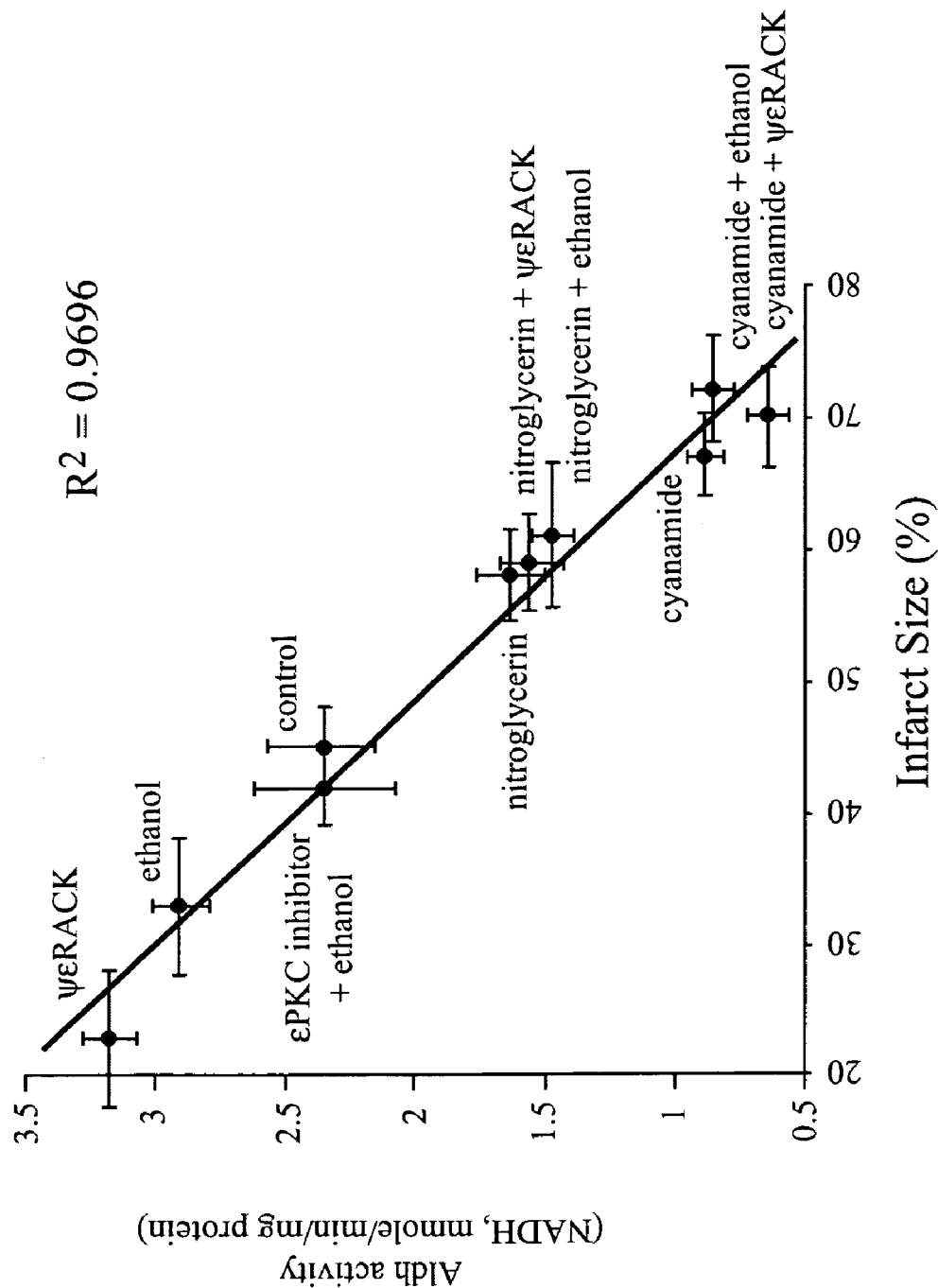
FIG. 8 depicts the inverse correlation between AldDH2 activity and infarct size.

FIG. 8: Inverse correlation between AldDH2 activity and infarct size. Based on the results from FIG. 7, an inverse correlation is observed between AldDH2 activity and infarct size with a regression coefficient of $R^2=0.9696$. This coefficient is obtained by plotting mean Aldh activity vs. mean infarct size from 10 different experimental treatment groups depicted in FIG. 7.

These results indicate an extremely strong inverse correlation ($R^2=0.9696$) between mitochondria aldehyde dehydrogenase (AldDH2) activity and infarct damage. In all conditions tested, increased AldDH2 activity invariably led to a smaller infarct size or lower creatine phosphate kinase release; conversely, reduced AldDH2 activity led to greater infarct damage or greater creatine phosphate kinase release. Examination of another cardiac enzyme marker, glucose-6-phosphate dehydrogenase, did not show such a correlation of infarct damage with this particular enzyme. This indicates that the correlation observed between AldDH2 activity and ischemia/reperfusion damage is specific. In addition, under normoxic condition, inhibition of AldDH2 activity by cyanamide did not lead to any greater cardiac damage as compared to the control group, indicating that AldDH2 plays an essential and critical role in protection against cell death only under ischemia/reperfusion condition. AldDH2 therefore is a critical enzymatic target that can be modulated to prevent ischemic tissue damage or increase susceptibility of cell/tissue to death caused by ischemia in diseases such as solid tumor.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The invention claimed is:

1. An in vitro method of identifying a candidate agent for treating an ischemic disorder, the method comprising:
 a) contacting a mitochondrial aldehyde dehydrogenase (AldDH2) polypeptide with a substrate for AldDH2; and a test agent, wherein the test agent is an organic compound that has a molecular weight of greater than 50 Daltons; and
 b) determining the effect of the test agent on increasing AldDH2 enzymatic activity, wherein a test agent that increases AldDH2 enzymatic activity is a candidate agent for treating an ischemic disorder.

2. The method of claim 1, wherein said determining step comprises measuring the level of NADH produced.

3. The method of claim 2, wherein said measuring comprises use of a fluorimetric assay.

4. The method of claim 1, wherein the AldDH2 is human AldDH2.

5. An in vitro method of identifying a candidate agent for the treatment of a solid tumor, the method comprising:
 a) contacting a mitochondrial aldehyde dehydrogenase (AldDH2) polypeptide with a substrate for AldDH2; and a test agent, wherein the test agent is an organic compound; and
 b) determining the effect of the test agent on inhibiting AldDH2 enzymatic activity, wherein a test agent that inhibits AldDH2 enzymatic activity is a test agent for the treatment of a solid tumor.

6. The method of claim 5, wherein said determining step comprises measuring the level of NADH produced.

7. The method of claim 6, wherein said measuring comprises use of a fluorimetric assay.

8. The method of claim 5, wherein the AldDH2 is human AldDH2.

* * * * *

UNITED STATES PATENT AND TRADEMARK OFFICE
CERTIFICATE OF CORRECTION

PATENT NO. : 7,560,241 B2
APPLICATION NO. : 11/008482
DATED : July 14, 2009
INVENTOR(S) : Mochly-Rosen et al.

Page 1 of 1

It is certified that error appears in the above-identified patent and that said Letters Patent is hereby corrected as shown below:

In the Specification Under Column 1:

• Please replace Column 1, line no. 13-16 with:

-- FEDERALLY-SPONSORED RESEARCH OR DEVELOPMENT
This invention was made with Government support under contract AA011147 awarded by the National Institutes of Health. The Government has certain rights in this invention. --

Signed and Sealed this
Seventeenth Day of September, 2013

Teresa Stanek Rea
*Deputy Director of the United States Patent and Trademark Office*